US00RE46190E

(19) United States
(12) Reissued Patent
Kitagawa et al.

(10) Patent Number: US RE46,190 E
(45) **Date of Reissued Patent: *Nov. 1, 2016**

(54) HIGH-MOLECULAR WEIGHT CONJUGATE OF STEROIDS

(71) Applicant: Nippon Kayaku Kabushiki Kaisha, Chiyoda-ku, Tokyo (JP)

(72) Inventors: Masayuki Kitagawa, Tokyo (JP); Toshitaka Murata, Tokyo (JP)

(73) Assignee: Nippon Kayaku Kabushiki Kaisha, Tokyo (JP)

( * ) Notice: This patent is subject to a terminal disclaimer.

(21) Appl. No.: 14/594,748

(22) Filed: Jan. 12, 2015

Related U.S. Patent Documents

Reissue of:
(64) Patent No.: 8,703,878
Issued: Apr. 22, 2014
Appl. No.: 12/678,620
PCT Filed: Sep. 26, 2008
PCT No.: PCT/JP2008/067413
§ 371 (c)(1),
(2) Date: Jun. 22, 2010
PCT Pub. No.: WO2009/041570
PCT Pub. Date: Apr. 2, 2009

(30) Foreign Application Priority Data

Sep. 28, 2007 (JP) ..... 2007-254904

(51) Int. Cl.
*A61K 47/48* (2006.01)
*A61K 31/785* (2006.01)

(52) U.S. Cl.
CPC ..... *A61K 31/785* (2013.01); *A61K 47/48215* (2013.01); *A61K 47/48315* (2013.01)

(58) Field of Classification Search
CPC ..... A61K 47/48
USPC ..... 525/240
See application file for complete search history.

(56) References Cited

U.S. PATENT DOCUMENTS 3,979,449 A 9/1976 Hirsbrunner et al.
4,011,317 A * 3/1977 Bertelli ..... C07J 41/005 514/179
4,734,512 A 3/1988 Kaneko et al.
4,892,733 A 1/1990 Bichon et al.
5,037,883 A 8/1991 Kopecek et al.
5,182,203 A 1/1993 Ebersole et al.
5,412,072 A * 5/1995 Sakurai et al. ..... 530/322
5,438,072 A 8/1995 Bobee et al.
5,510,103 A 4/1996 Yokoyama et al.
5,552,517 A * 9/1996 Martin ..... 528/363
5,571,889 A * 11/1996 Katoh et al. ..... 528/328
5,614,549 A 3/1997 Greenwald et al.
5,639,832 A 6/1997 Kroner et al.
5,693,751 A 12/1997 Sakurai et al.
5,877,205 A 3/1999 Andersson
5,985,548 A 11/1999 Collier et al.
6,025,385 A 2/2000 Shimizu et al.
6,107,333 A 8/2000 Andersson
6,153,655 A 11/2000 Martinez et al.
6,262,107 B1 7/2001 Li et al.
6,322,817 B1 11/2001 Maitra et al.
6,376,470 B1 4/2002 Greenwald et al.
6,410,731 B2 6/2002 Curran et al.
6,458,347 B1 * 10/2002 Sugawara et al. ..... 424/78.17
6,573,284 B1 6/2003 Riley et al.
6,596,757 B1 7/2003 Chari et al.
6,713,454 B1 3/2004 Ekwuribe et al.
6,720,304 B1 4/2004 Sinn et al.
6,720,306 B2 4/2004 Greenwald et al.
6,858,582 B2 2/2005 Yatvin et al.
7,138,490 B2 11/2006 Nakanishi et al.
7,176,185 B2 2/2007 Hilfinger et al.
7,495,099 B2 2/2009 Kitagawa et al.
7,700,709 B2 4/2010 Masuda et al.
7,820,759 B2 10/2010 Shimizu et al.
8,188,222 B2 5/2012 Yamamoto et al.
8,323,669 B2 12/2012 Kitagawa et al.
8,334,364 B2 12/2012 Yamamoto et al.
8,703,878 B2 4/2014 Kitagawa et al.
8,808,749 B2 8/2014 Kitagawa et al.
8,920,788 B2 * 12/2014 Kitagawa ..... A61K 31/197 424/486
8,940,332 B2 1/2015 Kitagawa et al.
9,018,323 B2 4/2015 Yamamoto et al.
9,149,540 B2 10/2015 Nakanishi et al.

(Continued)

FOREIGN PATENT DOCUMENTS

CA 2383240 A1 3/2001
CA 2334615 A1 8/2001

(Continued)

OTHER PUBLICATIONS

European communication dated Mar. 11, 2015 in co-pending European patent application No. 12830758.4.
Final Rejection mailed Apr. 21, 2015 in co-pending U.S. Appl. No. 14/241,924.
European communication mailed Apr. 21, 2015 in co-pending European patent application No. 07828587.1.
Chinese communication mailed Apr. 29, 2015 in co-pending Chinese patent application No. 201280043928.7.
Office Action mailed Jul. 7, 2015 in co-pending U.S. Appl. No. 11/662,834.
Final Rejection mailed Jul. 14, 2015 in co-pending U.S. Appl. No. 13/971,036.

(Continued)

*Primary Examiner* — Dwayne Jones
(74) *Attorney, Agent, or Firm* — Nields, Lemack & Frame, LLC

(57) ABSTRACT

Enzymes in the body vary among different species, and also vary among individuals of the same species. Thus, it has been demanded to develop a novel steroid-containing pharmaceutical preparation which can release a drug in a manner independent of the enzymes present in the body, and which is expected to have an efficacious therapeutic effect.
Disclosed is a high-molecular weight conjugate of a steroid, comprising a structure in which a carboxylic acid group of a polymer having a polyethylene glycol moiety and a succinic acid monoamide moiety having two or more succinic acid monoamide units is ester-bonded to a hydroxy group in the steroid.

10 Claims, 1 Drawing Sheet

(56) References Cited

U.S. PATENT DOCUMENTS

| | | | |
|---|---|---|---|
| 9,346,923 | B2 | 5/2016 | Yamamoto et al. |
| 2001/0003779 | A1 | 6/2001 | Curran et al. |
| 2001/0014354 | A1 | 8/2001 | Yokoyama et al. |
| 2001/0041189 | A1 | 11/2001 | Xu |
| 2002/0009426 | A1 | 1/2002 | Greenwald et al. |
| 2002/0016285 | A1 | 2/2002 | Bhatt et al. |
| 2002/0099013 | A1 | 7/2002 | Piccariello et al. |
| 2002/0119951 | A1 | 8/2002 | Seyedi et al. |
| 2002/0161062 | A1 | 10/2002 | Biermann et al. |
| 2002/0183259 | A1 | 12/2002 | Choe et al. |
| 2003/0032593 | A1 | 2/2003 | Wender et al. |
| 2003/0054977 | A1 | 3/2003 | Kumar et al. |
| 2003/0149003 | A1 | 8/2003 | Chaplin et al. |
| 2005/0054026 | A1 | 3/2005 | Atsushi et al. |
| 2005/0119193 | A1 | 6/2005 | Motoyama |
| 2005/0147617 | A1* | 7/2005 | Ji et al. ..... 424/178.1 |
| 2005/0171036 | A1 | 8/2005 | Arakawa et al. |
| 2006/0009622 | A1 | 1/2006 | Fuselier et al. |
| 2006/0057219 | A1 | 3/2006 | Nagasaki et al. |
| 2006/0067910 | A1 | 3/2006 | Kitagawa et al. |
| 2006/0099265 | A1 | 5/2006 | Shimizu et al. |
| 2006/0233883 | A1 | 10/2006 | Ishihara et al. |
| 2006/0258569 | A1 | 11/2006 | McTavish |
| 2007/0004674 | A1 | 1/2007 | Shiotsu et al. |
| 2007/0196497 | A1 | 8/2007 | Pouliquen et al. |
| 2008/0113028 | A1 | 5/2008 | Shimizu et al. |
| 2008/0145432 | A1 | 6/2008 | Kakizawa et al. |
| 2008/0221062 | A1 | 9/2008 | Miyamoto et al. |
| 2008/0269218 | A1 | 10/2008 | Kuramochi et al. |
| 2008/0280937 | A1 | 11/2008 | Leamon et al. |
| 2009/0012252 | A1 | 1/2009 | Masuda et al. |
| 2009/0156742 | A1 | 6/2009 | Shimizu et al. |
| 2009/0162313 | A1 | 6/2009 | Kitagawa et al. |
| 2009/0239782 | A1 | 9/2009 | Nakamura et al. |
| 2009/0275732 | A1 | 11/2009 | Hirotsu et al. |
| 2009/0281300 | A1 | 11/2009 | Yamamoto et al. |
| 2010/0004403 | A1 | 1/2010 | Kitagawa et al. |
| 2010/0029849 | A1 | 2/2010 | Yamamoto et al. |
| 2010/0234537 | A1 | 9/2010 | Kitagawa et al. |
| 2010/0292414 | A1 | 11/2010 | Kitagawa et al. |
| 2011/0136990 | A1 | 6/2011 | Harada et al. |
| 2011/0201754 | A1 | 8/2011 | Kitagawa |
| 2011/0294980 | A1 | 12/2011 | Nakanishi |
| 2012/0116051 | A1 | 5/2012 | Kitagawa et al. |
| 2013/0331517 | A1 | 12/2013 | Yamamoto et al. |
| 2014/0024703 | A1 | 1/2014 | Shimizu et al. |
| 2014/0142167 | A1 | 5/2014 | Shimizu et al. |
| 2014/0288244 | A1 | 9/2014 | Yamamoto et al. |
| 2015/0011715 | A1 | 1/2015 | Nakamura et al. |
| 2015/0259479 | A1 | 9/2015 | Shimizu et al. |

FOREIGN PATENT DOCUMENTS

| | | | |
|---|---|---|---|
| CN | 1307866 | A | 8/2001 |
| CN | 1708540 | A | 12/2005 |
| CN | 1761485 | A | 4/2006 |
| CN | 1800238 | A | 7/2006 |
| CN | 101023119 | A | 8/2007 |
| CN | 101808651 | A | 8/2010 |
| CN | 102037058 | A | 4/2011 |
| EP | 0397307 | A2 | 11/1990 |
| EP | 0583955 | A2 | 2/1994 |
| EP | 0757049 | A1 | 2/1997 |
| EP | 1127570 | A2 | 8/2001 |
| EP | 1489125 | A1 | 12/2004 |
| EP | 1580216 | A1 | 9/2005 |
| EP | 1604687 | A1 | 12/2005 |
| EP | 1792927 | A1 | 6/2007 |
| EP | 1 857 446 | A1 | 11/2007 |
| EP | 1857446 | A1 | 11/2007 |
| EP | 2258397 | A1 | 12/2010 |
| JP | 61-243026 | A | 10/1986 |
| JP | 62-96088 | A | 5/1987 |
| JP | 62-145093 | A | 6/1987 |
| JP | 63-10789 | A | 1/1988 |
| JP | 63-23884 | A | 2/1988 |
| JP | 63-502037 | A | 8/1988 |
| JP | 64-61422 | A | 3/1989 |
| JP | 64-61423 | A | 3/1989 |
| JP | 2-300133 | A | 12/1990 |
| JP | 5-955 | A | 1/1993 |
| JP | 5-117385 | A | 5/1993 |
| JP | 6-107565 | A | 4/1994 |
| JP | 6-206815 | A | 7/1994 |
| JP | 6-206830 | A | 7/1994 |
| JP | 6-206832 | A | 7/1994 |
| JP | 6-296088 | A | 10/1994 |
| JP | 6-310789 | A | 11/1994 |
| JP | 6-323884 | A | 11/1994 |
| JP | 6-329085 | A | 11/1994 |
| JP | 8-48766 | A | 2/1996 |
| JP | 8-503689 | A | 4/1996 |
| JP | 8-503689 | H | 4/1996 |
| JP | 8-507558 | A | 8/1996 |
| JP | 8-310970 | A | 11/1996 |
| JP | 2694923 | A | 9/1997 |
| JP | 2694923 | B2 | 12/1997 |
| JP | 10-513187 | A | 12/1998 |
| JP | 11-335267 | A | 12/1999 |
| JP | 2000-515132 | A | 11/2000 |
| JP | 2000-516948 | A | 12/2000 |
| JP | 2000-517304 | A | 12/2000 |
| JP | 2001-226294 | A | 8/2001 |
| JP | 3268913 | A | 1/2002 |
| JP | 2002-69184 | A | 3/2002 |
| JP | 2002-508400 | A | 3/2002 |
| JP | 3268913 | B2 | 3/2002 |
| JP | 2002-512265 | A | 4/2002 |
| JP | 3310000 | A | 5/2002 |
| JP | 3310000 | B2 | 7/2002 |
| JP | 2003-509385 | A | 3/2003 |
| JP | 2003-509386 | A | 3/2003 |
| JP | 2003-511349 | A | 3/2003 |
| JP | 2003-511423 | A | 3/2003 |
| JP | 2003-524028 | A | 8/2003 |
| JP | 2003-525238 | A | 8/2003 |
| JP | 2003-527443 | A | 9/2003 |
| JP | 2003-342167 | A | 12/2003 |
| JP | 2003-342168 | A | 12/2003 |
| JP | 2003-342269 | A | 12/2003 |
| JP | 2004-39869 | A | 2/2004 |
| JP | 2004-530736 | A | 10/2004 |
| JP | 2004-532289 | A | 10/2004 |
| JP | 2005-51922 | A | 2/2005 |
| JP | 2005-507912 | A | 3/2005 |
| JP | 2005-508832 | A | 4/2005 |
| JP | 2005-517675 | A | 6/2005 |
| JP | 2005-519122 | A | 6/2005 |
| JP | 2005-533026 | A | 11/2005 |
| JP | 2006-510627 | A | 3/2006 |
| JP | 2006-511571 | A | 4/2006 |
| JP | 2006-120914 | A | 5/2006 |
| JP | 2006-517572 | A | 7/2006 |
| JP | 2006-521367 | A | 9/2006 |
| JP | 2006-524673 | A | 11/2006 |
| JP | 2007-111211 | A | 5/2007 |
| JP | 2007-511586 | A | 5/2007 |
| JP | 2007-191643 | A | 8/2007 |
| JP | 2008-41610 | A | 2/2008 |
| TW | 200812572 | A | 3/2008 |
| WO | 93/24476 | A | 12/1993 |
| WO | 93/24476 | A1 | 12/1993 |
| WO | 96/23794 | A | 8/1996 |
| WO | 96/23794 | A1 | 8/1996 |
| WO | 97/38727 | A | 10/1997 |
| WO | 97/38727 | A1 | 10/1997 |
| WO | 98/02426 | A | 1/1998 |
| WO | 98/02426 | A1 | 1/1998 |
| WO | 98/07713 | A | 2/1998 |
| WO | 98/07713 | A1 | 2/1998 |
| WO | 98/08489 | A1 | 3/1998 |
| WO | 99/30727 | A1 | 6/1999 |
| WO | 99/53951 | A | 10/1999 |
| WO | 99/53951 | A1 | 10/1999 |

(56) References Cited

FOREIGN PATENT DOCUMENTS

| | | | |
|---|---|---|---|
| WO | 01/19361 | A2 | 3/2001 |
| WO | 01/19406 | A2 | 3/2001 |
| WO | 01/19407 | A2 | 3/2001 |
| WO | 01/26693 | A2 | 4/2001 |
| WO | 01/64198 | A2 | 9/2001 |
| WO | 01/70275 | A2 | 9/2001 |
| WO | 01/92584 | A1 | 12/2001 |
| WO | 02/06279 | A1 | 1/2002 |
| WO | 02/065986 | A2 | 8/2002 |
| WO | 02/065988 | A2 | 8/2002 |
| WO | 02/066066 | A1 | 8/2002 |
| WO | 03/000771 | A1 | 1/2003 |
| WO | 03/035008 | A2 | 5/2003 |
| WO | 03/055860 | A1 | 7/2003 |
| WO | 2004/039869 | A1 | 5/2004 |
| WO | 2004/050087 | A1 | 6/2004 |
| WO | 2004/056782 | A1 | 7/2004 |
| WO | 2004/072051 | A1 | 8/2004 |
| WO | 2004/082718 | A1 | 9/2004 |
| WO | 2004/096212 | A1 | 11/2004 |
| WO | 2005/000300 | A1 | 1/2005 |
| WO | 2005/018674 | A1 | 3/2005 |
| WO | 2005/066214 | A1 | 7/2005 |
| WO | 2006/033296 | A1 | 3/2006 |
| WO | 2006/055670 | A2 | 5/2006 |
| WO | 2006/055760 | A1 | 5/2006 |
| WO | 2006/095668 | A1 | 9/2006 |
| WO | 2006/095783 | A1 | 9/2006 |
| WO | 2006/101052 | A1 | 9/2006 |
| WO | 2006/115293 | A1 | 11/2006 |
| WO | 2006/120914 | A | 11/2006 |
| WO | 2006/120915 | A1 | 11/2006 |
| WO | 2007/022493 | A2 | 2/2007 |
| WO | 2007/080898 | A1 | 7/2007 |
| WO | 2007/111211 | A1 | 10/2007 |
| WO | 2007/135910 | A1 | 11/2007 |
| WO | 2008/010463 | A1 | 1/2008 |
| WO | 2008/041610 | A1 | 4/2008 |
| WO | 2008/056596 | A1 | 5/2008 |
| WO | 2008/056654 | A1 | 5/2008 |
| WO | 2009/041570 | A1 | 4/2009 |
| WO | 2009/116509 | A1 | 9/2009 |
| WO | 2009/142326 | A1 | 11/2009 |
| WO | 2010/131675 | A1 | 11/2010 |

OTHER PUBLICATIONS

Office Action mailed Jun. 22, 2015 in co-pending U.S. Appl. No. 14/727,912.
Final Rejection mailed May 28, 2015 in co-pending U.S. Appl. No. 14/497,703.
Notice of Allowance mailed May 28, 2015 in co-pending U.S. Appl. No. 12/991,041.
Arch. Pharm. (Weinheim), Jan. 1995, vol. 328, No. 10, pp. 737-738, "An Improved and Large Scale Synthesis of the Natural Coumarin Scopoletin", Hauer, et al.
Australian Communication issued May 29, 2015 in co-pending Australian patent application No. 2012305405.
Office action mailed Oct. 5, 2015 in co-pending U.S. Appl. No. 14/108,875.
Office action mailed Aug. 17, 2015 in co-pending U.S. Appl. No. 14/241,924.
Matsusaki et al.; "Stably-dispersed and Surface-functional Bionanoparticles Prepared by Self-assembling Amphipathic Polymers of Hydrophilic Poly(y-glutamic acid) Bearing Hydrophobic Amino Acids." 2004, The Chemical Society of Japan; Chemistry Letters, vol. 33, No. 4, pp. 398-399.
Taiwanese communication, with English translation, dated Sep. 10, 2015 in co-pending Taiwanese patent application No. 101133180.
6001 Chemical Abstracts, American Chemical Society, US, vol. 132, No. 2, Oct. 1, 2000, XP-002168038, 1 page abstract, "Polymer Micelle Compositions Containing Poorly Water-Soluble Drugs and their Preparation", Ichiro, et al.
Merriam-Webster's Collegiate Dictionary—11th Edition, 2004, 22 pages.
J. Org. Chem 2001, 66, 8135-8138, "Novel Syntheses of Cis and Trans Isomers of Combretastatin A-4", Gaukroger, et al.
Anti Cancer Drug Design, vol. 14, No. 6, Dec. 1999, ISSN 0266-9536, pp. 539-548, "Synthesis and antitumor activities of amino acid prodrugs of amino-combretastatins", Ohsumi, et al.
Journal of Pharmaceutical Sciences, vol. 92, No. 7, Jul. 2003, pp. 1343-1355, "MiniReview-Amphiphilic Block Copolymers for Drug Delivery", Adams, et al.
Chemistry and Biology, vol. 11, 787-797, Jun. 2004, "Targeting Wide-Range Oncogenic Transformation via PU24FCI, a Specific Inhibitor of Tumor Hsp90", Vilenchik, et al.
Office Action dated Jan. 21, 2009 in abandoned U.S. Appl. No. 10/548,998.
Office Action dated Apr. 17, 2009 in abandoned U.S. Appl. No. 10/548,998.
Office Action dated Jul. 10, 2009 in abandoned U.S. Appl. No. 10/548,998.
Final Rejection dated Mar. 4, 2010 in abandoned U.S. Appl. No. 10/548,998.
Office Action mailed Oct. 7, 2013 in abandoned U.S. Appl. No. 10/548,998.
Office Action dated Nov. 12, 2010 in co-pending U.S. Appl. No. 11/662,834.
Office Action mailed Dec. 15, 2011 in co-pending U.S. Appl. No. 11/662,834.
Office Action mailed Aug. 25, 2014 in co-pending U.S. Appl. No. 11/662,834.
Final Rejection mailed Mar. 4, 2015 in co-pending U.S. Appl. No. 11/662,834.
Office Action mailed Dec. 31, 2014 in co-pending U.S. Appl. No. 13/971,036.
Office Action dated Jul. 21, 2010 in abandoned U.S. Appl. No. 12/309,061.
Final Rejection dated Feb. 28, 2011 in abandoned U.S. Appl. No. 12/309,061.
Office Action dated Apr. 4, 2011 in abandoned U.S. Appl. No. 12/311,086.
Final Rejection dated Jul. 27, 2011 in abandoned U.S. Appl. No. 12/311,086.
Office Action mailed Apr. 18, 2013 in abandoned U.S. Appl. No. 12/311,086.
Final Rejection mailed Aug. 28, 2013 in abandoned U.S. Appl. No. 12/311,086.
Examiner's Answer to Appeal Brief mailed Jul. 29, 2014 in abandoned U.S. Appl. No. 12/311,086.
Office Action mailed Nov. 24, 2014 in co-pending U.S. Appl. No. 14/497,703.
Office Action mailed Apr. 25, 2012 in corresponding U.S. Appl. No. 12/678,620.
Final Rejection mailed Oct. 17, 2012 in corresponding U.S. Appl. No. 12/678,620.
Notice of Allowance mailed Jan. 16, 2014 in corresponding U.S. Appl. No. 12/678,620.
Office Action—Restriction—mailed Jul. 11, 2012 in co-pending U.S. Appl. No. 12/991,041.
Notice of Allowance mailed Jan. 28, 2015 in co-pending U.S. Appl. No. 13/884,413.
Office Action mailed Oct. 1, 2014 in co-pending U.S. Appl. No. 14/241,924.
Journal of Peptide Science, vol. 3 (1997), 141-144, "Evaluation of Carbodiimides Using a Competition Method", Izdebski, et al.
Bioorganic & Medicinal Chemistry Letters, 2005, vol. 15, 3338-3343, "The identification, synthesis, protein crystal structure and in vitro biochemical evaluation of a new 3,4-diarylpyrazole class of Hsp90 inhibitors", Cheung, et al.
Molecular Cancer Therapeutics 2006, vol. 5, 1628-1637, "Preclinical pharmacokinetics and metabolism of a novel diaryl pyrazole resorcinol series of heat shock protein 90 inhibitors", Smith, et al.
Registry Entry for Registry No. 171009-07-07, which entered STN on Dec. 6, 1995, 3 pages.

(56) References Cited

OTHER PUBLICATIONS

Merriam Webster Online Dictionary entry for "Derivative", (http://www.merriam-webster.com/dictionary/derivative), last accessed Feb. 9, 2011, 3 pages.
Colloids and Surfaces B: Biointerfaces V 16 (1999) pp. 217-226, "Micelle-like structures of poly(ethyleneoxide)-block-poly(2-hydroxyethyl aspartamide)-methotrexate conjugates", Li, et al.
Pharmaceutical Research, V. 17, No. 5 (2000) pp. 607-611, "Methotrexate Esters of Poly(EthyleneOxide)-Block-Poly(2-Hydroxyethyl-L-Aspartamide). Part I: Effects of the Level of Methotrexate Conjugation on the Stability of Micelles and on Drug Release", Li, et al.
English translation of JP 6-206815 (Jul. 26, 1994), "Pharmaceutical Preparation Based on Block Copolymer-Anticancer Drug Complex", by Masayuki Yokoyama, et al., 24 pages, US Patent and Trademark Office, Aug. 2007, Translated by: FLS, Inc.
International Search Report dated Dec. 24, 2003 in PCT application No. PCT/JP03/13838.
Taiwanese Communication dated Nov. 30, 2006 in Taiwanese patent application No. TW092130275.
Russian Communication dated Apr. 20, 2007 in Russian patent application No. RU2005116309.
European Communication dated Sep. 25, 2008 in European patent application No. EP03769949.3.
International Search Report dated May 11, 2004 in co-pending PCT application No. PCT/JP2004/003647.
Chinese Communicaton dated Oct. 20, 2006 in co-pending Chinese patent application No. CN200480007329.5.
Russian Communication dated Jun. 27, 2007 in co-pending Russian patent application No. RU2005132309/04.
European Communication dated Feb. 17, 2009 in co-pending European patent application No. EP04721673.4.
Chinese Communication dated Apr. 17, 2009 in co-pending Chinese patent application No. CN200480007329.5.
European Communication dated Jun. 5, 2009 in co-pending European patent application No. EP04721673.4.
Korean Communication dated Nov. 8, 2010 in co-pending Korean patent application No. 10-2005-7017245.
International Search Report dated Nov. 15, 2005 in co-pending PCT application No. PCT/JP2005/017127.
Taiwanese Communication dated Jul. 22, 2011 in co-pending Taiwanese patent application No. 094132581.
European Communication dated Oct. 28, 2011 in co-pending European Patent Application No. EP 05783310.5.
Taiwanese Communication dated Dec. 14, 2011 in co-pending Taiwanese patent application No. 094132581.
International Search Report dated Jul. 25, 2006 in PCT application No. PCT/JP2006/308826.
International Search Report dated May 15, 2007 in PCT application No. PCT/JP2007/055809.
International Search Report dated Aug. 21, 2007 in PCT application No. PCT/JP2007/060026.
European Communication dated Oct. 23, 2009 in European patent application No. EP07743461.1.
Chinese Communication dated Aug. 11, 2010 in Chinese patent application No. CN2007800177809.
Russian Communication dated May 16, 2011 in Russian patent application No. RU2008149932/04.
Chinese Communication dated Sep. 23, 2011 in Chinese patent application No. 2007800177809.
Australian Communication dated Oct. 28, 2011 in Australian Patent Application No. 2007252678.
International Search Report dated Oct. 16, 2007 in PCT application No. PCT/JP2007/063990.
Chinese Communication dated Nov. 10, 2010 in Chinese application No. CN 200780027210.8.
International Search Report dated Jan. 8, 2008 in PCT application No. PCT/JP2007/068841.
International Preliminary Report on Patentability issued Apr. 7, 2009 and Apr. 22, 2009 in co-pending PCT application No. PCT/JP2007/068841.
Japanese Communication mailed Mar. 26, 2013 in co-pending Japanese Patent Application No. 2008-537500.
International Search Report dated Jan. 29, 2008 in PCT application No. PCT/JP2007/071532.
European Communication mailed Jan. 27, 2012 in European Patent Application No. 07831039.8.
International Search Report dated Jan. 29, 2008 in PCT application No. PCT/JP2007/071305.
International Search Report dated Dec. 9, 2008 in corresponding PCT application No. PCT/JP2008/067413.
Chinese Communication dated Oct. 10, 2011 in corresponding Chinese Patent Application No. 200880109404.7.
Japanese Communication mailed May 14, 2013 in corresponding Japanese patent application No. JP 2009-534401.
International Search Report mailed Jun. 23, 2009 in PCT application No. PCT/JP2009/055115.
Chinese Communication dated Aug. 31, 2011 in Chinese patent application No. 200980110087.5.
European Communication mailed May 24, 2013 in European patent application No. 09722008.1
Japanese communication mailed Sep. 24, 2013 in Japanese patent application No. JP 2010-503871.
Japanese communication mailed Jul. 8, 2014 in co-pending Japanese patent application No. 2010-503871.
Chinese Communication mailed Dec. 31, 2013 in Chinese patent application No. CN 200980110087.5.
Chinese communication mailed Jun. 17, 2014 in Chinese patent application No. 200980110087.5.
International Search Report dated Jul. 21, 2009 in co-pending PCT application No. PCT/JP2009/058325.
European communication dated Oct. 29, 2014 in co-pending European patent application No. 09742696.9.
International Search Report dated Aug. 10, 2010 in PCT application No. PCT/JP2010/058034.
Chinese Communication mailed Feb. 22, 2013 in Chinese Patent Application No. 201080021960.6.
International Search Report mailed Dec. 4, 2012 in co-pending PCT application No. PCT/JP2012/072160.
Written Opinion mailed Dec. 4, 2012 in co-pending PCT application No. PCT/JP2012/072160.
International Preliminary Report on Patentability mailed Mar. 20, 2014 in co-pending PCT application No. PCT/JP2012/072160.
Trends in Molecular Medicine, vol. 8, No. 4, (Supp.) 2002, p. S55-61, "Hsp90 Inhibitors as Novel Cancer Chemotherapeutic Agents", Neckers.
Current Cancer Drug Targets, 2003, vol. 3, 385-390, "The Clinical Applications of Heat Shock Protein Inhibitors in Cancer—Present and Future", Banerji, et al.
Cancer Science, Feb. 2004, V. 95, No. 2, 105-111, "Antitumor Activity of Sugar-Modified Cytosine Nucleosides", Matsuda, et al.
Cancer Research vol. 44, Jan. 25-30, 1984, "Antitumor Activity of 1-B-D-Arabinofuranosylcytosine Conjugated with Polyglutamic Acid and its Derivative", Kato, et al.
Journal of Controlled Release vol. 79 (2002), 55-70, "Anticancer Drug Delivery Systems: Multi-Loaded N4-acyl poly(ethylene glycol) prodrugs of ara-C. II. Efficacy in ascites and solid tumors", Choe, et al.
J. of Pharmacokinetics and BioPharmaceutics, vol. 23, No. 4, 1995, pp. 397-406, "In Vivo Pharmacokinetic Study for the Assessment of Poly(L-Aspartic Acid) as a Drug Carrier for Colon-Specific Drug Delivery", Leopold, et al.
Advanced Drug Delivery Reviews, vol. 20, (1996), 195-201, "Limethason as a lipid microsphere preparation: An Overview", Yokoyama, et al.
Notice of Allowance mailed Jul. 1, 2016 in co-pending U.S. Appl. No. 13/971,036.
Chinese communication, with English translation, dated Jan. 12, 2016 in co-pending Chinese patent application No. 201280043928.7.

(56) References Cited

OTHER PUBLICATIONS

Russian communication, with English translation, dated Jan. 28, 2016 in co-pending Russian patent application No. 2014114264.
Final rejection mailed Jan. 29, 2016 in co-pending U.S. Appl. No. 11/662,834.
Final rejection mailed Jan. 15, 2016 in co-pending U.S. Appl. No. 14/727,912.
Final rejection mailed Apr. 6, 2016 in co-pending U.S. Appl. No. 14/108,875.
Notice of Allowance mailed Jan. 29, 2016 in co-pending U.S. Appl. No. 14/241,924.
European Communication, dated Oct. 28, 2011 in co-pending European Patent Application No. EP 05783310.5.
Australian Communication, dated Oct. 28, 2011 in co-pending Australian Patent No. 2007252678.
Chinese Communication, with English translation, dated Oct. 10, 2011 in corresponding Chinese Patent Application No. 200880109404.7.
Office Action dated Dec. 15, 2011 in co-pending U.S. Appl. No. 11/662,834.
Chinese Office Action dated Nov. 10, 2010 in co-pending U.S. Appl. No. 12/309,061, filed Mar. 3, 2009 /Foreign Application No. 200780027210.8.
Korean Office Action dated Nov. 8, 2010 in co-pending U.S. Appl. No. 10/548,998, filed Oct. 31, 2005 /Foreign Application No. 10-2005-7017245.
Office Action dated Sep. 9, 2011 in co-pending U.S. Appl. No. 12/226,962.
Colloids and Surfaces B: Biointerfaces V. 16 (1999) pp. 217-226, "Micelle-like structures of poly(ethyleneoxide)-block-poly(2-hydroxethyl aspartamide)-methotrexate conjugates", Li, et al.
Pharmaceutical Research, V. 17, No. 5 (2000), pp. 607-611, "Methotrexate Esters of Poly (EthyleneOxide)-Block-Poly(2-Hydroxyethyl-L-Aspartamide). Part I: Effects of the Level of Methotrexate Conjugation on the Stability of Micelles and on Drug Release", Li, et al.
International Search Report dated Jul. 21, 2009 in co-pending international patent application No. PCT/JP2009/058325.
Taiwan Communication, with English translation, dated Jul. 22, 2011 in co-pending Taiwan Patent Application No. 094132581.
Office Action dated Oct. 12, 2011 in co-pending U.S. Appl. No. 12/312,157.
International Search Report dated Dec. 24, 2003 in U.S. Pat. No. 7,495,099 (PCT/JP03/13838).
Taiwanese communication dated Nov. 30, 2006 in U.S. Pat. No. 7,495,099 (TW092130275).
Russian communication dated Apr. 20, 2007 in U.S. Pat. No. 7,495,099 (RU2005116309/04).
European communication dated Sep. 25, 2008 in U.S. Pat. No. 7,495,099 (EP03769949.3).
International Search Report dated May 11, 2004 in co-pending U.S. Appl. No. 10/548,998 (PCT/JP2004/003647).
Chinese communication dated Oct. 20, 2006 in co-pending U.S. Appl. No. 10/548,998 (CN200480007329.5).
Russian communication dated Jun. 27, 2007 in co-pending U.S. Appl. No. 10/548,998 (RU2005132309/04).
European communication dated Feb. 17, 2009 in co-pending U.S. Appl. No. 10/548,998 (EP04721673.4).
Chinese communication dated Apr. 17, 2009 in co-pending U.S. Appl. No. 10/548,998 (CN200480007329.5).
European communication dated Jun. 5, 2009 in co-pending U.S. Appl. No. 10/548,998 (EP04721673.4).
International Search Report dated Nov. 15, 2005 in co-pending U.S. Appl. No. 12/322,322 (PCT/JP2005/017127).
International Search Report dated Jul. 25, 2006 in U.S. Pat. No. 7,700,709 (PCT/JP2006/308826).
International Search Report dated May 15, 2007 in co-pending U.S. Appl. No. 12/225,230 (PCT/JP20071055809).
International Search Report dated Aug. 21, 2007 in co-pending U.S. Appl. No. 12/226,962 (PCT/JP2007/060026).
European communication dated Oct. 23, 2009 in co-pending U.S. Appl. No. 12/226,962 (EP07743461.1).
International Search Report dated Oct. 16, 2007 in co-pending U.S. Appl. No. 12/309,061 (PCT/JP2007/063990).
International Search Report dated Jan. 8, 2008 in co-pending U.S. Appl. No. 12/311,086 (PCT/JP2007/068841).
International Search Report dated Jan. 29, 2008 in co-pending U.S. Appl. No. 12/312,009 (PCT/JP2007/071532).
Office Actions dated Jan. 21, 2009, Apr. 17, 2009, Jul. 10, 2009, Mar. 4, 2010 in co-pending U.S. Appl. No. 10/548,998.
Office Actions dated Oct. 19, 2009, Mar. 19, 2010, Jun. 23, 2010, Jul. 7, 2010 in co-pending U.S. Appl. No. 12/322,322.
Office Action dated Aug. 24, 2010 in co-pending U.S. Appl. No. 11/662,834.
Office Actions dated Jul. 21, 2010 in co-pending U.S. Appl. No. 12/309,061.
A.V. Shur, "High-Molecular Weight Compounds"; Course for Universities, Third Edition, Revised and supplemented, "Visshaja Shkola" Publishing House, 1981, 656 pages, see p. 265.
Chemical Abstracts, 6001, vol. 132; Oct. 10, 2000 No. 2—XP-002168038.
Merriam-Webster's Collegiate Dictionary—Eleventh Edition 2004.
J. Org. Chem. 2001, 66, 8135-8138; Keirs Gaukroger, et al.; "Novel Synthesis of Cis and Trans Isomers of Combretastatin A-4".
Anti-Cancer Drug Design; vol. 14, No. 6, Dec. 1999—ISSN 0266-9536.
Journal of Pharmaceutical Sciences, vol. 92, No. 7, Jul. 2003; Monica L. Adams et al.; "MiniReview—Amphiphilic Block Copolymers for Drug Delivery".
Chemistry and Biology, vol. 11, 787-797, Jun. 2004; Maria Vilenchick et al.; "Targeting Wide-Range Oncogenic Transformation via PU24FCI, a specific Inhibitor of Tumor Hsp90".
Trends in Molecular Medicine vol. 8, No. 4 (Suppl.) 2002; Len Neckers; "Hsp90 inhibitors as novel cancer chemotherapeutic agents".
Current Cancer Drug Targets, 2003, 3, 385-390; Udai Banerji et al.; "The Clinical Applications of Heat Shock Protein Inhibitors in Cancer Present and Future".
Cancer Sci; Feb. 2004; vol. 95; No. 2; 105-111; Akira Matsuda et al.; "Antitumor Activity of Sugar-Modified Cytosine Nucleosides".
Cancer Research 44, Jan. 25-30, 1984; Yoshinori Kato et al.; "Anti-tumor Activity of 1-B-D-Arabinofuranosylcytosine Conjugated with Polyglutamic Acid and Its Derivative".
Journal of Controlled Release 79 (2002) 55-70; Yun H. Choe et al.; "Anticancer Drug Delivery Systems: Multi-Loaded N4-acyl poly-(ethylene glycol) prodrugs of ara-C. II Efficacy in ascites and solid tumors".
Journal of Pharmacokinetics and Biopharmaceutics, vol. 23, No. 4, 1995; Claudia S. Leopold; In vivo Pharmacokinetic Study for the Assessment of Poly(L-Aspartic Acid) as a Drug Carrier for Colon-Specific Drug Delivery).
International Search Report dated Dec. 9, 2008 in co-pending U.S. Appl. No. 12/678,620 (PCT/JP2008/067413).
Bioorganic & Medicinal Chemistry Letters 15 (2005) pp. 3338-3343, "The identification, synthesis, protein crystal structure and in vitro biochemical evaluation of a new 3,4-diarylpyrazole class of Hsp90 inhibitors", Cheung, et al.
Molecular Cancer Therapeutics, 2006, 5(6), Jun. 2006, pp. 1628-1637, "Preclinical pharmacokinetics and metabolism of a novel diaryl pyrazole resorcinol series of heat shock protein 90 inhibitors", Smith, et al.
Registry Entry for Registry No. 171009-07-7, which entered STN on Dec. 6, 1995, 3 pages.
Registry Entry for Registry No. 7689-03-4, which entered STN on Nov. 16, 1984, 3 pages.
Merriam-Webster Online Dictionary entry for "Derivative", (http://www.merriam-webster.com/dictionary/derivative), last accessed Feb. 9, 2011, 3 pages.
Office Action dated dated Apr. 4, 2011 in co-pending U.S. Appl. No. 12/311,086.
Final Rejection dated Feb. 28, 2011 in co-pending U.S. Appl. No. 12/309,061.

(56) References Cited

OTHER PUBLICATIONS

Chinese communication dated Aug. 11, 2010 in co-pending foreign application (CN2007800177809).
Office Action dated Nov. 12, 2010 in a co-pending U.S. Appl. No. 11/662,834.
Journal of Peptide Science, vol. 3, 141-144 (1997); Jan Izdebski et al.; "Evaluation of Carbodiimides Using A Competition Method".
Taiwanese Communication, with English translation, dated Dec. 14, 2011 in co-pending Taiwanese Application No. 094132581.
International Search Report dated Aug. 10, 2010 in co-pending PCT application No. PCT/JP2010/058034.
Final Rejection dated Feb. 16, 2012 in co-pending U.S. Appl. No. 12/226,962.
Office Action dated Feb. 21, 2012 in co-pending U.S. Appl. No. 12/312,009.
Notice of Allowance dated Mar. 1, 2012 in co-pending U.S. Appl. No. 12/312,157.
Final Rejection dated Jun. 8, 2011 in co-pending U.S. Appl. No. 11/662,834.
Office Action dated Jun. 16, 2011 in co-pending U.S. Appl. No. 12/225,230.
Final Rejection dated Jul. 27, 2011 in co-pending U.S. Appl. No. 12/311,086.
Russian Communication, with English translation, dated May 16, 2011 in co-pending foreign patent application No. RU 2008149932/04.
Advanced Drug Delivery Reviews 20 (1996) 1995-201; K. Yokoyama et al.; "Limethason as a lipid microsphere preparation: An overview".
International Search Report dated Jan. 29, 2008 in co-pending U.S. Appl. No. 12/312,009 (PCT/JP2007/071305).
International Search Report dated Jan. 29, 2008 in co-pending U.S. Appl. No. 12/312,157 (PCT/JP200/071532).
Office Action mailed Oct. 25, 2011 in co-pending U.S. Appl. No. 12/312,009.
Final Rejection mailed Nov. 8, 2011 in co-pending U.S. Appl. No. 12/225,230.
Chinese Communication, with English translation, dated Sep. 23, 2011 in co-pending Chinese patent application No. 2007800177809.
Journal of Controlled Release, 2001, V. 74, No. 1-3, pp. 295-302, paragraph of "2. Structure of NK911", "Development of the polymer micelle carrier system for doxorubicin", Nakanishi, et al.
International Search Report mailed Jun. 23, 2009 in co-pending PCT application No. PCT/JP2009/055115.
Chinese Communication, with English translation, dated Aug. 31, 2011 in co-pending Chinese patent application No. 200980110087.5.
Canadian Communication issued Jun. 26, 2013 in co-pending Canadian patent application No. CA 2,664,852.
International Preliminary Report on Patentability, with English translation, issued Apr. 7, 2009 and Apr. 22, 2009 in co-pending PCT application No. PCT/JP2007/068841.
Final Rejection mailed Aug. 28, 2013 in co-pending U.S. Appl. No. 12/311,086.
Office Action mailed Sep. 6, 2013 in co-pending U.S. Appl. No. 12/922,747.
The Merck Index, Fourteenth Edition, 2006, p. 1-16, O'Neil, et al.
Advanced Drug Delivery Reviews, vol. 55, No. 2, Feb. 2003, pp. 217-250, "Effective drug delivery by PEGylated drug conjugates", Greenwald, et al.
European Communication mailed May 24, 2013 in co-pending European patent application No. 09722008.1.
Office Action mailed Jun. 12, 2013 in co-pending U.S. Appl. No. 13/319,175.
Final Rejection mailed Mar. 5, 2013 in co-pending U.S. Appl. No. 12/922,747.
Final Rejection mailed Mar. 28, 2013 in co-pending U.S. Appl. No. 12/991,041.
Chinese Communication, with English translation, mailed Feb. 22, 2013 in co-pending Chinese Patent Application No. 201080021960.6.
Office Action mailed Apr. 18, 2013 in co-pending U.S. Appl. No. 12/311,086.
Office Action mailed Apr. 6, 2012 in co-pending U.S. Appl. No. 12/225,230.
Miscellaneous Communication mailed Mar. 19, 2012 in co-pending U.S. Appl. No. 12/312,157.
Office Action-Restriction—mailed Apr. 27, 2012 in co-pending U.S. Appl. No. 12/922,747.
Japanese Communication, with English translation, mailed Mar. 26, 2013 in co-pending Japanese Patent Application No. 2008-537500.
International Search Report and Written Opinion mailed Jan. 24, 2012 in co-pending PCT application No. PCT/JP2011/076373.
Japanese Communication, with partial English translation, mailed May 14, 2013 in corresponding Japanese patent application No. JP 2009-534401.
Office Action-Restriction—mailed Jan. 29, 2013 in co-pending U.S. Appl. No. 13/319,175.
Final Rejection mailed Aug. 21, 2012 in co-pending U.S. Appl. No. 11/662,834.
Notice of Allowance mailed Aug. 28, 2012 in co-pending U.S. Appl. No. 12/225,230.
Notice of Allowance mailed Aug. 7, 2012 in co-pending U.S. Appl. No. 12/312,009.
Office Action mailed Jul. 30, 2012 in co-pending U.S. Appl. No. 12/922,747.
Office Action-Restriction—mailed Jul. 11, 2012 in co-pending U.S. Appl. No. 12/991,041.
Office Action mailed Aug. 22, 2012 in co-pending U.S. Appl. No. 12/991,041.
Japanese communication, with English translation, mailed Sep. 24, 2013 in co-pending Japanese patent application No. JP2010-503871.
Office Action mailed Oct. 7, 2013 in co-pending U.S. Appl. No. 10/548,998.
European Communication mailed Jan. 27, 2012 in co-pending European Patent Application No. 07831039.8.
Antimicrobial Agents and Chemotherapy, vol. 2, No. 5, Nov. 1972, pp. 395-401, XP 55016709, ISSN: 0066-4804, "Antiviral Action of Camptothecin", Horwitz, et al.
Final Rejection mailed Jan. 10, 2014 in co-pending U.S. Appl. No. 13/319,175.

* cited by examiner

HIGH-MOLECULAR WEIGHT CONJUGATE OF STEROIDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

The present invention relates to a high-molecular weight conjugate of steroids in which a carboxylic acid group of a polymer having a polyethylene glycol moiety and a succinic acid monoamide moiety is ester-bonded to a hydroxy group in the steroids, a method for producing the same, and the use thereof.

BACKGROUND ART

Steroid pharmaceuticals are a therapeutic agent for various disorders including many inflammatory disorders such as rheumatism and collagen disease, allergic diseases, serious infections and cancer, and they have excellent therapeutic effects on these disorders. However, when they are prescribed for a certain disorder, various actions of steroids are manifested as side effects on normal sites other than lesions to be treated, and as a result a dosage amount may be limited in some cases. In addition, it is easily expected that the longer it remains on a lesion, the more efficacious the steroid would be on the lesion. However, due to the concern regarding the side effect as described above, the number of repeated doses may be also limited. In other words, although the steroids are an excellent pharmaceutical compound which exhibits efficacy in treating various disorders, the use of steroids tends to be avoided at clinical settings due to their side effects. Currently, as an attempt to solve this problem, studies, for example, to accumulate the steroids selectively on a lesion and to release them at the lesion over a long period of time are carried out.

One of such studies relates to a drug delivery system, and as an example of the system, Limethasone (manufactured by Mitsubishi Pharma Corporation), which comprises palmitic acid ester of dexamethasone in a lipid sphere is known in the art (Adv. Drug Delivery Rev., vol. 20, p. 195 (1996)).

Patent Document 1 describes a formulation comprising nano particles of phosphoric acid ester of betamethasone formed with zinc, polylactic acid, and polyethylene glycol-polylactic acid.

Meanwhile, Patent Document 2 discloses a polymer compound comprising a drug bonded to a block copolymer of polyethylene glycol and polyaspartic acid, which forms micelles and has water solubility. Patent Document 3 describes a polymer derivative of camptothecins in which a side chain carboxylic acid group of a block copolymer of polyethylene glycol and polyglutamic acid is bonded to a phenolic hydroxy group of camptothecins. It is known that these polymer compounds accumulate in tumors due to an EPR effect. However, neither Patent Document 2 nor Patent Document 3 discloses a polymer compound to which steroids are bonded.

[Patent Document 1] Japanese Patent Application Laid-open Publication (Kohyo) No. 2006-521367

[Patent Document 2] Japanese Patent Publication No. 2694923

[Patent Document 3] WO 2004/39869

[Non-Patent Document 1] Adv. Drug Delivery Rev., vol. 20, p. 195 (1996)

DISCLOSURE OF THE INVENTION

Problems to be Solved by the Invention

Limethasone described above releases palmitic acid ester of dexamethasone from lipid spheres, and then steroids produced by hydrolysis of the ester bond by enzymes in the body exhibit their activity. Similarly, the nano particles described in Patent Document 1 release phosphoric acid ester of betamethasone from the particles, and then steroids produced by hydrolysis of the ester bond by enzymes in the body exhibit their activity. However, it has been known that activities of hydrolyzing enzymes in the body vary not only among different species but also among individuals of the same species, and thus there is also a concern that the effect of the drug release from the conjugate would be greatly different among individuals when the cleavage of the bond to drug depends on the hydrolyzing enzymes.

In the case of the adriamycin conjugate described in Patent Document 2 in which a block copolymer is bonded to adriamycin via an amide bond, the efficacy is questionable since the release of the drug by hydrolysis is slow due to the amide bond, a chemically stable bonding form.

Although steroids including prednisolone, methyl prednisolone, dexamethasone, betamethasone, clobetasol, diflorasone, diflucortolone, fluocinolone acetonide, hydrocortisone, difluprednate, beclometasone, triamcinolone and alclometasone are a useful drug for treating disorders such as rheumatism, asthma, nephritis. ulcerative colitis, autoimmune diseases, allergy, psoriasis, eczema, stomatits, granuloma and malignant lymphoma, the side effects are very frequently manifested. Thus, there has been a demand for a novel drug which does not depend on hydrolyzing enzymes present in the body and delivers the steroids only to desired site to manifest fewer side effects.

Means for Solving the Problems

The inventors of the present invention noticed the higher permeability of blood vessels around cancer lesions or inflammation sites, and, as a consequence of studies to solve the problems described above. we considered that, as result of the circulation in the body of a drug administered in the vessels, the drug would be more easily accumulated in cancer lesions or inflammation sites around which the vessels are highly permeable. Consequently, they achieved an invention of a high-molecular weight conjugate of steroids in which the steroids are chemically bonded to a polymer carrier of a block copolymer including polyethylene glycol. The high-molecular weight conjugate of steroids can also be used as a prodrug.

Efficacy of conventional prodrugs may be likely to vary among individuals as the hydrolyzing enzymes of a patient are used for the release of the drug. On the other hand, the present invention, by introducing a moiety of succinic acid monoamide bonded to steroids into a polymer, intends to chemically hydrolyze the conjugate under physiological condition. Specifically, the inventors found a phenomenon that a compound having a hydroxy group is easily released as the structure of succinic acid monoamide changes to a cyclized structure (i.e., succinic imide) when the compound having a hydroxy group is ester-bonded to a free carboxylic acid of succinic acid monoamide, and attempted to apply the phenomenon to a block copolymer including polyethylene glycol. As a result, they have found that, in the high-molecular weight derivative of steroids in which a polymer having a polyethylene glycol moiety and a succinic acid monoamide moiety is ester-bonded to a hydroxy group of the steroids having a hydroxy group, the ester bond can be cleaved without depending on hydrolyzing enzymes to release the steroids that are the active entities and to exhibit the pharmacological effects and have completed the present invention.

Specifically, the present invention is related to the following (1) to (14).

(1) A high-molecular weight conjugate of steroids, comprising a structure in which a carboxylic acid group of a polymer having a polyethylene glycol moiety and a succinic acid monoamide moiety having two or more succinic acid monoamide units is ester-bonded to a hydroxy group in the steroids.

(2) The high-molecular weight conjugate of steroids according to (1) above, wherein the polymer having a polyethylene glycol moiety and a succinic acid monoamide moiety is a block copolymer.

(3) The high-molecular weight conjugate of steroids according to (1) or (2) above, wherein the succinic acid monoamide moiety is polyaspartic acid.

(4) The high-molecular weight conjugate of steroids according to any one of (1) to (3) above represented by formula (I)

[

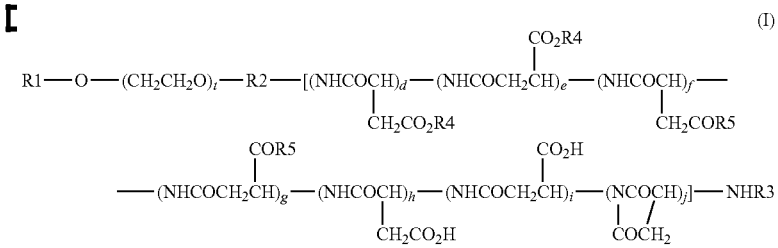

(I)

]

(I)

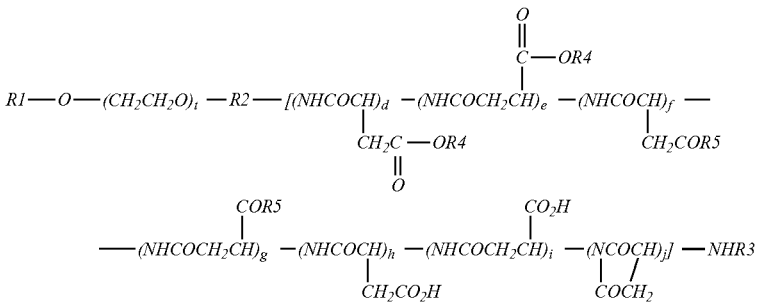

wherein R1 represents a hydrogen atom or a (C1-C6) alkyl group; R2 represents a linking group; R3 represents a hydrogen atom or a (C1-C6) acyl group; [R4 represents a residue of the hydroxy group of the] *—OR4 represents an alcoholic hydroxy group of said* steroids; R5 represents a group selected from the group consisting of a (C1-C30) alkoxy group, a (C7-C30) aralkyloxy group, a (C1-C30) alkylamino group, a di(C1-C30) alkylamino group, an amino acid with a protected carboxy group and —N(R6) CONH(R7) wherein R6 and R7, which may be identical or different from each other, represent a (C3-C6) cyclic alkyl group or a (C1-C5) alkyl group which may be substituted with a tertiary amine group; t represents an integer from 5 to 11500; and d, e, f, g, h, i or j each independently represents an integer from 0 to 200; provided that d+e represents an integer from 1 to 200, d+e+f+g+h+i+j represents an integer from 3 to 200; and respective units of the polyaspartic acid are bonded in any order.

(5) The high-molecular weight conjugate of steroids according to (4) above, wherein R1 represents a (C1-C6) alkyl group, R2 represents a (C2-C6) alkylene group, R3 represents a (C1-C6) acyl group, t represents an integer of 100 to 300, and d, e, f, g, h, i or j each independently represents an integer from 0 to 100, provided that d+e represents an integer from 1 to 100 and d+e+f+g+h+i+j represents an integer from 6 to 100.

(6) The high-molecular weight conjugate of steroids according to (5) above, wherein R1 represents a (C1-C3) alkyl group, R2 represents a (C2-C4) alkylene group, R3 represents a (C1-C3) acyl group, t represents an integer from 100 to 300, and d, e, f, g, h, i or j each independently represents an integer from 0 to 90, provided that d+e represents an integer from 1 to 90 and d+e+f+g+h+i+j represents an integer from 15 to 90.

(7) The high-molecular weight conjugate of steroids according to any one of (1) to (6) above, in which the steroids are prednisolone, methyl prednisolone, dexamethasone, betamethasone, clobetasol, diflorasone, diflucortolone, fluocinolone acetonide, hydrocortisone, difluprednate, beclometasone, triamcinolone or alclometasone.

(8) A high-molecular weight conjugate of steroids which is obtained by ester-bonding a carboxylic acid group of a polymer having a polyethylene glycol moiety and a succinic acid monoamide moiety having two or more succinic acid monoamide units to a hydroxy group in the steroids having hydroxy groups by using a dehydrating condensation agent in an organic solvent.

(9) A method of manufacturing the high-molecular weight conjugate of steroids described in any one of (1) to (7)

above, the method comprising ester-bonding a carboxylic acid group of a polymer having a polyethylene glycol moiety and a succinic acid monoamide moiety having two or more succinic acid monoamide units to a hydroxy group of the steroids having the hydroxy group, by using a dehydrating condensation agent in an organic solvent.

(10) A pharmaceutical composition comprising as an active ingredient the high-molecular weight conjugate of steroids according to any one of (1) to (8) above.

(11) An anti-inflammatory agent comprising as an active ingredient the high-molecular weight conjugate of steroids according to any one of (1) to (8) above.

(12) An anti-rheumatism agent comprising as an active ingredient the high-molecular weight conjugate of steroids according to any one of (1) to (8) above.

(13) An agent for treating collagen disease comprising as an active ingredient the high-molecular weight conjugate of steroids according to any one of (1) to (8) above.

(14) An anti-allergy agent comprising as an active ingredient the high-molecular weight conjugate of steroids according to any one of (1) to (8) above.

Effect of the Invention

The high-molecular weight conjugate of steroids of the present invention can deliver the steroids only to a desired site and release the steroids without depending on hydrolyzing enzymes in the body. Thus, without being affected by difference among individuals, the steroids are expected to achieve efficacious therapeutic effects.

BEST MODE FOR CARRYING OUT THE INVENTION

The high-molecular weight conjugate of steroids of the present invention is characterized in that a carboxylic acid group of a polymer having a polyethylene glycol moiety and a succinic acid monoamide moiety having two or more succinic acid monoamide units is ester-bonded to a hydroxy group in the steroids.

According to the present invention, the term "succinic acid monoamide moiety" refers to the structure of —HNCO—C—C—$CO_2H$, and examples thereof include succinic acid monoamide (—HNCO—$CH_2$—$CH_2$—$CO_2H$) and a structure in which one of the two carboxylic acid groups of aspartic acid is amidated (—HNCO—CH(—NH—)—$CH_2$—$CO_2H$ or —HNCO—$CH_2$—CH(—NH—)—$CO_2H$). These succinic acid monoamide moieties may constitute a polymer backbone, for example, as in the case of polyaspartic acid, or may be bound to a functional group of the backbone polymer composed of a polyalcohol such as dextran, a polyamine such as polylysine, or a polycarboxylic acid other than polyaspartic acid (for example, polylactic acid, etc.).

Examples of the polymer having a polyethylene glycol moiety and a succinic acid monoamide moiety having two or more succinic acid monoamide units include a graft-type polymer in which the polyethylene glycol moiety and the succinic acid monoamide moiety branch from the polymer backbone in a comb-like form, and a block-type polymer (block copolymer) in which the polymers having a polyethylene glycol moiety and a succinic acid monoamide moiety are tandemly aligned.

When the succinic acid monoamide moiety forms polyaspartic acid, the graft-type polymer also includes a polymer in which the polyethylene glycol moiety is partially bonded to the polyaspartic acid backbone. The block-type polymer includes a polymer in which the terminal of polyaspartic acid is bonded to the terminal of polyethylene glycol moiety.

The polyethylene glycol moiety in the polymer of the high-molecular weight conjugate of steroids of the present invention includes polyethylene glycol in which both terminals or a single terminal is modified. When both terminals are modified, the modifying groups can be identical or different from each other. Examples of the modifying group include a (C1-C6) alkyl group optionally having a substituent group. Examples of the alkyl group of the (C1-C6) alkyl group optionally having a substituent group include an alkyl group set forth as R1 in Formula (I) below. Preferred is a (C1-C4) alkyl group including, for example, a methyl group, an ethyl group, an n-propyl group and an n-butyl group. Examples of a substituent group included in the (C1-C6) alkyl group optionally having a substituent group include, for example, an amino group, a methylamino group, a dimethylamino group, an ethylamino group and a diethylamino group.

The molecular weight of the polyethylene glycol moiety is about 300 to 500,000, preferably about 500 to 100,000, more preferably about 1,000 to 50,000.

The molecular weight of the polymer having a polyethylene glycol moiety and a succinic acid monoamide moiety is about 500 to 600,000, preferably about 600 to 110,000, more preferably about 800 to 80,000.

According to the present invention, the term "molecular weight" refers to the weight average molecular weight determined by the GPC method.

In the high-molecular weight conjugate of steroids of the present invention, the amount of the steroids bonded to the polymer having a polyethylene glycol moiety and a succinic acid monoamide moiety having two or more succinic acid monoamide units is 1 to 100%, preferably 1 to 90%, more preferably 2 to 60%, based on the total number of carboxylic acid groups.

According to the present invention, the steroids are not particularly limited, provided that they are the steroids having an alcoholic hydroxy group. Examples the steroids include prednisolone represented by the following formula (II), methyl prednisolone represented by the following formula (III), dexamethasone represented by the following formula (IV), betamethasone represented by the following formula (V), clobetasol represented by the following formula (VI), diflorasone represented by the following formula (VII), diflucortolone represented by the following formula (VIII), fluocinolone acetonide represented by the following formula (IX), hydrocortisone represented by the following formula (X), a deacylated product of difluprednate represented by the following formula (XI), beclometasone represented by the following formula (XII), triamcinolone represented by the following formula (XIII) and alclometasone represented by the following formula (XIV). Preferably, examples of the hydroxy group of steroids include, for example, a primary hydroxy group of prednisolone represented by the following formula (II) or a secondary hydroxy group of clobetasol represented by the following formula (VI). However, the position for substitution is not limited.

(II)
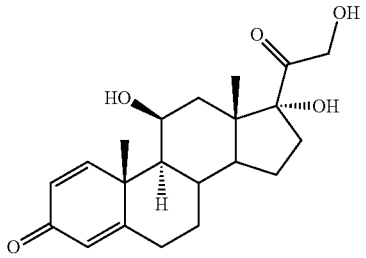
(III)
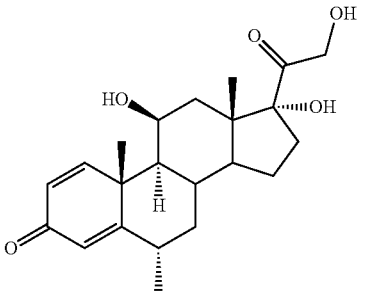
(IV)
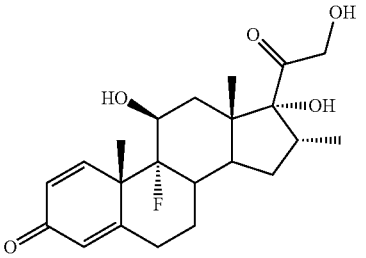
(V)
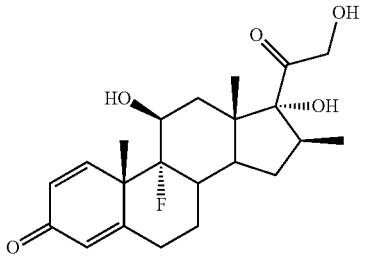
(VI)
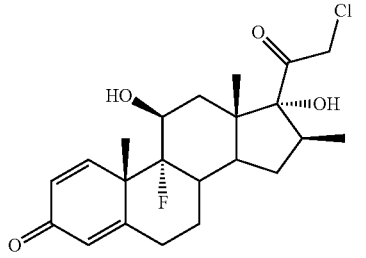
-continued
(VII)
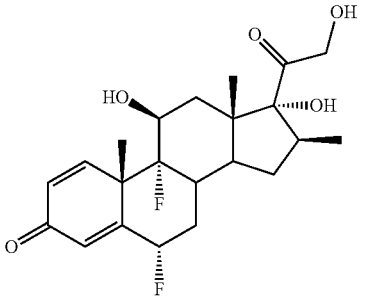
(VIII)
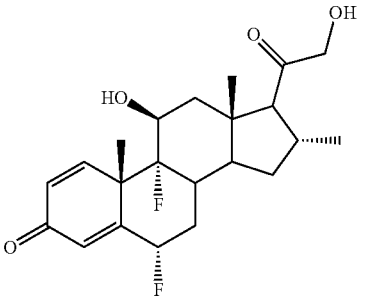
(IX)
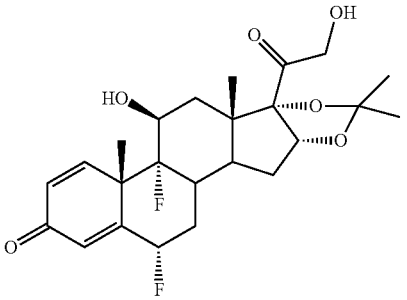
(X)
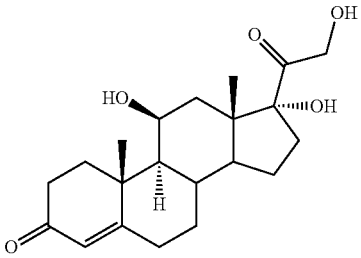
(XI)
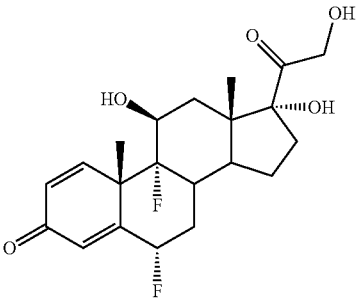

-continued (XII)

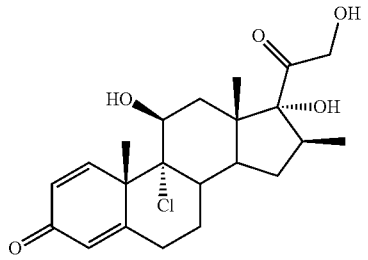

(XIII)

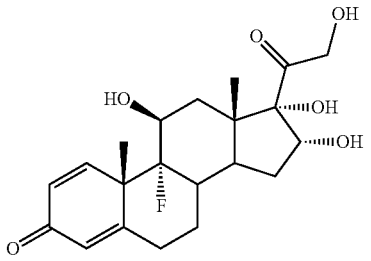

(XIV)

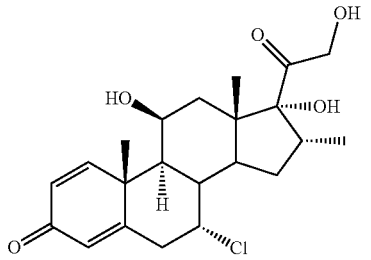

The steroids indicated above and derivatives thereof are commercially available as an anti-allergic agent, an anti-inflammatory agent, an agent for treating autoimmune diseases, an anti-tumor agent, etc.

According to the present invention, the succinic acid monoamide moiety having two or more succinic acid monoamide units is preferably polyaspartic acid.

A preferred high-molecular weight conjugate of steroids of the present invention includes a compound represented by formula (I) above, wherein R1 represents a hydrogen atom or a (C1-C6) alkyl group; R2 represents a linking group; R3 represents a hydrogen atom or a (C1-C6) acyl group; [R4 represents a residue of the hydroxy group of the] *—OR4 represents an alcoholic hydroxy group of said* steroids; R5 represents a group selected from the group consisting of a (C1-C30) alkoxy group, a (C7-C30) aralkyloxy group, a (C1-C30) alkylamino group, a di(C1-C30) alkylamino group, an amino acid with protected carboxy group and —N(R6)CONH(R7) wherein R6 and R7, which may be identical or different from each other, represent a (C3-C6) cyclic alkyl group or a (C1-C5) alkyl group which may be substituted with a tertiary amine group; t represents an integer from 5 to 11,500; and d, e, f, g, h, i or j each independently represents an integer from 0 to 200; provided that d+e represents an integer from 1 to 200 and that d+e+f+g+h+i+j represents an integer from 3 to 200.

Examples of the (C1-C6) alkyl group for R1 in the general formula (I) include a straight-chain or branched (C1-C6) alkyl group, including a methyl group, an ethyl group, an n-propyl group, an i-propyl group, an n-butyl group and a t-butyl group. Preferred is a straight-chain or branched (C1-C4) alkyl group, and particularly preferred is a straight-chain or branched (C1-C3) alkyl group including a methyl group, an ethyl group, an n-propyl group, and an i-propyl group, and more particularly preferred is a methyl group.

Examples of the linking group represented by R2 in the general formula (I) include, but are not particularly limited to, a (C2-C6) alkylene group. Preferred is a (C2-C4) alkylene group including, for example, an ethylene group, a trimethylene group and a tetramethylene group, and particularly preferred is a trimethylene group.

Examples of the (C1-C6) acyl group for R3 in the general formula (I) include, but not particularly limited to, a formyl group, an acetyl group, a propionyl group and a pivaloyl group. Preferred is a (C1-C3) acyl group, and more preferred is an acetyl group.

With regard to the [residue of the hydroxy group of the steroids for R4 ] *alcoholic hydroxy group of the steroids for —OR4* in the general formula (I), examples of the steroids include the steroids enumerated above.

R5 in the general formula (I) represents a group selected from the group consisting of a (C1-C30) alkoxy group, a (C7-C30) aralkyloxy group, a (C1-C30) alkylamino group, a di(C1-C30) alkylamino group, an amino acid with protected carboxy group, and —N(R6)CONH(R7) wherein R6 and R7, which may be identical or different from each other, represent a (C3-C6) cyclic alkyl group or a (C1-C5) alkyl group which may be substituted with a tertiary amino group. R5 in the general formula (I) may be identical or different from each other in one molecule, and a polymer in the high-molecular weight conjugate of steroids may include a single-type R5 or mixed type R5.

A substituent group can be introduced to R5 as necessary. Physical properties of the high-molecular weight conjugate of steroids can be controlled by the introduction of the substituent groups to R5. For example, the release rate of the steroids can be freely controlled.

Examples of the (C1-C30) alkoxy group include a straight-chain or branched (C1-C30) alkoxy group, and preferred is a straight-chain or branched (C1-C10) alkoxy group, including, for example, a methoxy group, an ethoxy group, an n-propoxy group, an i-propoxy group, an n-butoxy group and a t-butoxy group. Examples of the (C7-C30) aralkyloxy group include a straight-chain or branched (C7-C30) aralkyloxy group, and preferred is a straight-chain or branched (C7-C12) aralkyloxy group, including, for example, a 4-phenylbutoxy group.

Examples of the (C1-C30) alkylamino group or di(C1-C30) alkylamino group include a straight-chain or branched (C1-C30) alkylamino group or a straight-chain or branched di(C1-C30) alkylamino group, and preferred is a straight-chain or branched (C1-C20) alkylamino group or a straight-chain or branched di(C1-C20) alkylamino group, including, for example, an methylamino group, an ethyl amino group, an n-propylamino group, an i-propylamino group, an n-butylamino group, a t-butylamino group, a dimethylamino group, a diethylamino group and a dibutylamino group.

Examples of the amino acid with protected carboxy group include an amino acid generally used in peptide synthesis, in which a carboxyl group is protected, including, for example, a phenylalanine benzyl ester.

Examples of the group —N(R6) CONH(R7) for R5 in the general formula (I), wherein R6 and R7, which may be identical or different from each other, represent a (C3-C6) cyclic alkyl group or a (C1-C5) alkyl group optionally substituted with a tertiary amine group include. but not particularly limited to, for example, a cyclohexylaminocarbonylcyclohexylamino group and an isopropylaminocarbonylisopropylamino group.

Polyaspartic acid which is a succinic acid monoamide moiety in the high-molecular weight conjugate of steroids represented by the general formula (I) of the present invention, includes constituent units of α-amino acid type, β-amino acid type and cyclized type. These constituent units are bound in any order, and may be bound to form a block-type form or a random-type form.

The total number of aspartic acid residues in the high-molecular weight conjugate of steroids represented by the aforementioned general formula (I) is represented by "d+e+f+g+h+i+j", and is about 3 to 200, preferably about 6 to 100, more preferably about 15 to 90.

The proportion of the number of aspartic acid residues bonded to the steroids (d+e) based on the total number of aspartic acid residues (d+e+f+g+h+i+j) is 1 to 100%, preferably 3 to 90%, more preferably 4 to 60%. In addition, the number of aspartic acid residues (d+e) is about 1 to 200, preferably about 1 to 100, more preferably about 1 to 90.

The proportion of α-amino acid type (d+f+h) based on the total number of aspartic acid residues (d+e+f+g+h+i+j) is 10 to 100%, preferably 20 to 100%. The proportion can be appropriately changed, for example, by suitably selecting a deprotection condition for a protecting group in the polyaspartic acid which was produced by using the protecting group.

In the aforementioned general formula (I), t is an integer from about 5 to 11,500, preferably an integer from about 8 to 2300, more preferably, an integer from about 100 to 300.

The high-molecular weight conjugate of steroids of the present invention represented by the aforementioned general formula (I) may form micelles with the polyethylene glycol moiety as the outer shell in water.

The high-molecular weight conjugate of steroids of the present invention is obtained by ester-bonding a carboxylic acid group of a polymer having a polyethylene glycol moiety and a succinic acid monoamide moiety having two or more succinic acid monoamide units to a hydroxy group of steroids by using a dehydrating condensation agent in an organic solvent, and the present invention also includes this manufacturing method; that is, a manufacturing method of subjecting, for example, a block copolymer of a polyethylene glycol moiety-polyaspartic acid produced by the method described in Japanese Patent Application Laid-Open No. 6-206815, and steroids in which the functional groups other than the group to be reacted are protected as necessary, to a reaction using a dehydrating condensation agent such as dicyclohexylcarbodiimide (DCC), diisopropylcarbodiimide (DIPC), 1-ethyl-3-(3-dimethylaminopropyl) carbodiimide hydrochloride salt (WSC) and 1-ethoxycarbonyl-2-ethoxy-1,2-dihydroxyquinolinone (EEDQ) at a temperature of 0 to 180° C., preferably 5 to 50° C. in an organic solvent in which both of the block copolymer and the steroids are dissolved, preferably in an aprotic polar solvent such as N,N-dimethylformamide (DMF), 1,3-dimethyl-2-imidazolidinone (DMI) and N-methylpyrrolidone (NMP). Furthermore, a reaction aid such as N,N-dimethylaminopyridine (DMAP) may also be used for the condensation reaction. After condensation reaction, deprotection is carried out as necessary, and conventional operations for separation and purification, etc., are applied to obtain a high-molecular weight conjugate of steroids.

In addition, a high-molecular weight conjugate of steroids in which R5 is a —N(R6)CONH(R7) group wherein R6 and R7, which may be identical or different from each other, represent a (C3-C6) cyclic alkyl group or a (C1-C5) alkyl group optionally substituted with a tertiary amine group may also be obtained by a reaction using the aforementioned carbodiimides as an condensation agent.

As a method of introducing as R5 a (C1-C30) alkoxy group, a (C7-C30) aralkyloxy group, a (C1-C30) alkylamino group, a di(C1-C30) alkylamino group or an amino acid with protected carboxy group into a compound of the general formula (I), there can be mentioned a method in which a carboxylic acid of the polymer is first activated according to the aforementioned method, and then reacted with a corresponding alcohol, a corresponding amine or an amino acid with protected carboxy group in a an amount to be introduced under basic conditions; and a method in which a corresponding alcohol, a corresponding amine or an amino acid with a protected carboxy group is first activated, and then reacted with a polymer. After purification of the polymer, it is also possible to re-activate any unreacted carboxylic acid groups of the polymer by the same reaction, and the re-activated carboxylic acid groups may be condensed with the hydroxyl group of the steroids. Alternatively, different alcohols, amines, etc. are repeatedly reacted to synthesize a mixture of polymers having various substituents as R5, with which the hydroxy group of steroids may subsequently condensed. Furthermore, after condensation of steroids, a (C1-C30) alkoxy group, a (C7-C30) aralkyloxy group, a (C1-C30) alkylamino group, a di(C1-C30) alkylamino group or an amino acid with protected carboxy group may be introduced.

However, the method of manufacturing the high-molecular weight conjugate of steroids of the present invention is not intended to be limited to the aforementioned methods.

The high-molecular weight conjugate of steroids of the present invention releases steroids under the condition in the body to exhibit the pharmacological activity of the steroids, and therefore functioning as a drug, it can be used as an anti-inflammatory agent, an anti-rheumatism agent, an agent for treating collagen disease, an anti-allergic agent, an anti-cancer agent, etc. The high-molecular weight conjugate of steroids of the present invention can be used in a dosage form which is conventionally used, including, for example, injections, tablets, powders and the like. For formulation process, a pharmaceutically acceptable carriers which are conventionally used, for example, binding agents, lubricating agents, disintegrating agents, solvents, vehicles, solubilizing agents, dispersing agents, stabilizing agents. suspending agents, preservatives, soothing agents, colorants and flavors can also be used. Among various dosage forms, the use as an injection is preferred, and usually, for example, water, physiological saline, 5% glucose or mannitol solution, water-soluble organic solvent (for example. glycerol, ethanol, dimethylsulfoxide, N-methylpyrrolidone, polyethylene glycol, Cremophor and the like, or a mixture thereof), or a mixture of water and water-soluble organic solvents can be used.

The dosage of the high-molecular weight conjugate of steroids of the present invention can varies as a matter of course, depending on sex, age, physiological conditions, pathology and the like of patients. It is parenterally administered, typically at a does of 0.01 to 500 mg/m$^2$, preferably 0.1 to 250 mg/m$^2$, as an active ingredient per day. Administration by injection is carried out intravenously, intraarterially, to the affected site (inflammation site), for example.

EXAMPLES

Hereinafter, the present invention will be illustrated more specifically with reference to Examples, but is not intended to be limited to the Examples. Conditions for analysis by HPLC (high performance liquid chromatography) is as follows:

column: ODS (inertsil ODS-3 4.6×150 mm)
detection: UV 254 nm
elution: A) 0.1% aqueous phosphate solution,
B) acetonitrile/1% aqueous phosphate solution (9/1)
B %=30%.

Example 1

Synthesis of Compound 1 (conjugate of prednisolone and a block copolymer consisting of methoxypolyethylene glycol moiety having molecular weight of 12,000 and polyaspartic acid moiety having a polymerization number of 33: in the general formula (I), R1=Me (methyl group), R2=trimethylene group, R3=Ac (acetyl group), [R4=prednisolone residue] —*OR4=the alcoholic hydroxy group of prednisolone*, R5=isopropylaminocarbonyliso propylamino group, d+e+f+g+h+i+j=33, t=273)

An N-acetylated product of a copolymer of polyethylene glycol with methoxy at one terminal-polyaspartic acid (a block copolymer consisting of a methoxypolyethylene glycol moiety having a molecular weight of 12,000 and a polyaspartic acid moiety having a polymerization number of 33, and in the general formula (I), R1=Me (methyl group), R2=trimethylene group, R3=Ac (acetyl group), d=e=f=g=j=0; 265 mg) produced according to the production method described in Japanese Patent Application Laid-open No. 6-206815, and commercially available prednisolone (manufactured by Tokyo Chemical Industry Co., Ltd.; 100 mg) were dissolved in DMF (3.7 ml), and DMAP (7 mg) and DIPC (0.2 ml) were added thereto. The mixture was stirred for 40 hrs at 15° C. To the reaction solution, ethanol (5.6 ml), ethyl acetate (5.6 ml) and diisopropyl ether (45 ml) were added, and the mixture was stirred for 3 hrs at room temperature. Subsequently, the precipitate was collected by filtration and washed with ethanol/diisopropyl ether (1/4 (v/v); 10 ml). The resulting precipitate was dissolved in acetonitrile/water (1/1 (v/v); 20 ml), and then the solution was applied to a column of an ion exchange resin (DOWEX50 ($H^+$), manufactured by The Dow Chemical Company; 3 ml), and then eluted with acetonitrile/water (1/1 (v/v); 6 ml). After water (20 ml) was added to the eluted fraction thus obtained, acetonitrile was distilled off under reduced pressure, and then the residue was freeze-dried to obtain Compound 1 (340 mg).

On the basis of the amount of unreacted prednisolone present in the reaction liquid determined by HPLC (high performance liquid chromatography), the content of prednisolone in Compound 1 was determined as 25.4% (w/w), and the proportion of d+e based on d+e+f+g+h+i+j was determined as 44%. In Compound 1, free prednisolone was not detected.

According to this method, an isopropylaminocarbonylisopropylamino group can be added as R5, and the abundance ratio of the group was determined by $^1$H-NMR (hydrogen nuclear magnetic resonance spectrum) using Compound 1 dissolved in sodium deuteroxide/deuterium oxide/deuterated acetonitrile. The proportion of isopropylaminocarbonylisopropylamino group to polyaspartic acid of Compound 1, that is, the proportion of f+g based on d+e+f+g+h+i+j was 9%. The remaining aspartic acid residues are in the form of a free carboxylic acid (corresponding to h+i) or a cyclic structure (corresponding to j).

Example 2

Synthesis of Compound 2 (conjugate of dexamethasone and a block copolymer consisting of a methoxypolyethylene glycol moiety having a molecular weight of 12,000 and a polyaspartic acid moiety having a polymerization number of 35: in the general formula (I), R1=Me (methyl group), R2=trimethylene group, R3=Ac (acetyl group), [R4=dexamethasone residue] —*OR4= the alcoholic hydroxy group of dexamethasone*, R5=isopropylaminocarbonyl isopropyl amino group, d+e+f+g+h+i+j=35, t=273)

An N-acetylated product of a copolymer of polyethylene glycol with methoxy at one terminal-polyaspartic acid produced according to the manufacturing method described in Japanese Patent Application Laid-open No. 6-206815 (a polymerization number of aspartic acid is 35; 100 mg) and commercially available prednisolone (manufactured by Tokyo Chemical Industry Co., Ltd.; 42 mg) were dissolved in DMF (2.0 ml), and DMAP in a DMF solution (0.773 mmol/ml solution, 27.7 μl) and DIPC (67.0 μl) were added thereto. The mixture was stirred for 43 hrs at 15° C. DIPC (17.0 μl) was further added and stirred for 4 hrs at 30° C. To the reaction solution, ethyl acetate (4.0 ml) and diisopropyl ether (16 ml) were added, and the mixture was stirred for 3 hrs at room temperature. Subsequently, the precipitate was collected by filtration and washed with ethyl acetate/diisopropyl ether (1/4 (v/v); 10 ml). The resulting precipitate was dissolved in acetonitrile/water (1/1 (v/v); 12 ml), and then the solution was applied to a column of an ion exchange resin (DOWEX50 ($H^+$), manufactured by The Dow Chemical Company; 10 ml) and eluted with acetonitrile/water (1/1 (v/v); 20 ml). Acetonitrile in the eluted fraction thus obtained was distilled off under reduced pressure, and the residue was freeze-dried to obtain Compound 2 (108 mg).

Compound 2 was collected and treated with alkali to cleave the bonded dexamethasone. By HPLC (high performance liquid chromatography), the content of dexamethasone in Compound 2 was determined as 20.7% (w/w) and the proportion of d+e based on d+e+f+g+h+i+j was determined as 31%. In the isolated Compound 2, free dexamethasone was found to be 0.3% (w/w).

Example 3

Synthesis of Compound 3 (conjugate of dexamethasone and a block copolymer consisting of a methoxypolyethylene glycol moiety having a molecular weight of 12,000 and a polyaspartic acid moiety having a polymerization number of 35 to which phenylalanine benzyl ester is further bonded: in the general formula (I), R1=Me (methyl group), R2=trimethylene group, R3=Ac (acetyl group), [R4=dexamethasone residue] —*OR4=the alcoholic hydroxy group of dexamethasone*, R5=phenylalanine benzyl ester and isopropylaminocarbonylisopropylamino group, d+e+f+g+h+i+j=35, t=273)

An N-acetylated product of methoxypolyethylene glycol with methoxy at one terminal-polyaspartic acid copolymer (polymerization number of aspartic acid 35; 100 mg) prepared according to the manufacturing method described in Japanese Patent Application Laid-open No. 6-206815 and commercially available dexamethasone (manufactured by Tokyo Chemical Industry Co., Ltd.; 42 mg) were dissolved in DMF (2.0 ml), and DMAP in a DMF solution (0.773 mmol/ml solution, 27.7 μl) and DIPC (33.5 μl) were added thereto. The mixture was stirred for 20 hrs at 15° C. To the reaction solution, a DMF solution of phenylalanine benzyl ester (0.612 mmol/ml, 140.0 μl) and DIPC (33.5 μl) were further added and stirred for 23 hrs at 30° C. Thereafter, DIPC (17.0 μl) was further added, and the mixture was stirred for 4 hrs at 30° C. To the reaction liquid, ethyl acetate (4.0 ml) and diisopropyl ether (16 ml) were added. After stirring for 3 hrs at room temperature, the precipitate was collected by filtration and washed with ethyl acetate/diisopropyl ether (1/4 (v/v); 10 ml). The resulting precipitate was dissolved in acetonitrile/water (1/1 (v/v); 12 ml), and the solution was applied to a column of an ion exchange resin (DOWEX50 ($H^+$), manufactured by The Dow Chemical Company; 10 ml), and then eluted with acetonitrile/water (1/1 (v/v); 20 ml). Acetonitrile in the eluted fraction thus obtained was distilled off under reduced pressure, and the residue was freeze-dried to obtain Compound 3 (112 mg).

Compound 3 was collected and treated with alkali to cleave the bonded dexamethasone. By HPLC (high performance liquid chromatography), the content of dexamethasone in Compound 3 was determined as 20.5% (w/w). In the isolated Compound 3, free dexamethasone was found to be 0.2% (w/w).

Comparative Example 1

Synthesis of Comparative compound 1 (conjugate of prednisolone and a block copolymer consisting of methoxypolyethylene glycol moiety having molecular weight of 12,000 and polyglutamic acid moiety having a polymerization number of 23)

An N-acetylated product of polyethylene glycol with methoxy at one terminal-polyglutamic acid copolymer (a block copolymer consisting of a methoxypolyethylene glycol moiety having a molecular weight of 12,000 and a polyglutamic acid moiety having a polymerization number of 23; 128 mg) prepared according to the manufacturing method described in Japanese Patent Application Laid-Open publication No. 5-955 and commercially available prednisolone (50 mg) were dissolved in DMF (1.3 ml), and DMAP (2.4 mg) and DIPC (0.06 ml) were added thereto. The mixture was stirred for 20 hrs at 25° C. To the reaction solution, ethanol (2 ml), ethyl acetate (2 ml) and diisopropyl ether (12 ml) were added, and the mixture was stirred for 30 minutes at room temperature. Subsequently, the precipitate was collected by filtration and washed with ethanol/diisopropyl ether (1/4 (v/v); 2 ml). The resulting precipitate was dissolved in acetonitrile/water (1/1 (v/v); 7 ml) and applied to a column of anion exchange resin (DOWEX50 ($H^+$), manufactured by The Dow Chemical Company; 1 ml), and then eluted with acetonitrile/water (1/1 (v/v); 2 ml). After water (10 ml) was added to the eluted fraction thus obtained, acetonitrile was distilled off under reduced pressure, and then the residue was freeze-dried to obtain Comparative compound 1 (160 mg).

On the basis of the amount of unreacted prednisolone present in the reaction solution determined by HPLC (high performance liquid chromatography), the content of prednisolone in Comparative compound 1 was determined as 25.8% (w/w). In the isolated Comparative compound 1, no free prednisolone was detected.

Test Example

Drug Release in the Absence of Enzymes

Compound 1 or Comparative compound 1, or Compound 2 or Compound 3 was dissolved in PBS (phosphate buffered physiological saline; pH 7.1) to a polymer concentration of 1 mg/ml, and the solution was incubated at 37° C. Prednisolone or dexamethasone released from Compound 1, Compound 2, Compound 3 or Comparative compound 1 was separated and quantified by HPLC in comparison with a standard curve. The proportion of the quantified value based on the total amount of the drug determined from the drug content in the high-molecular weight conjugate is shown in FIGS. 1 and 2.

As shown in FIG. 1, the high-molecular weight conjugate of the present invention (Compound 1) released almost 98% of prednisolone within 24 hrs even in the absence of hydrolyzing enzymes. However, Comparative compound 1 including no succinic acid monoamide moiety hardly released prednisolone even after 24 hrs.

As shown in FIG. 2, the high-molecular weight conjugate of the present invention (Compounds 2 and 3) was found to be capable of releasing almost 60 to 90% of dexamethasone within 24 hrs even in the absence of hydrolyzing enzymes. It was also shown that the linking of phenylalanine benzyl ester to the high-molecular weight conjugate allowed to control the release rate of dexamethasone.

These results demonstrate the excellent drug release performance of the high-molecular weight conjugate of steroids of the present invention under a neutral condition even in the absence of enzymes, and thus a capability of the high-molecular weight conjugate of steroids of the present invention to release steroid under a physiological condition observed, for example, in blood or body fluids. It is further demonstrated that, the appropriate linking of a substituent group including, for example, phenylalanine benzyl ester, allows to control the release rate.

BRIEF DESCRIPTION OF THE DRAWINGS

In FIG. 1, -●- indicates the proportion of the drug released from Compound 1 of the present invention, and -○- indicates the proportion of the drug released from Comparative compound 1.

In FIG. 2, -▲- indicates the proportion of the drug released from Compound 2 of the present invention, and -■- indicates the proportion of the drug released from Compound 3 of the present invention.

Figure 1:
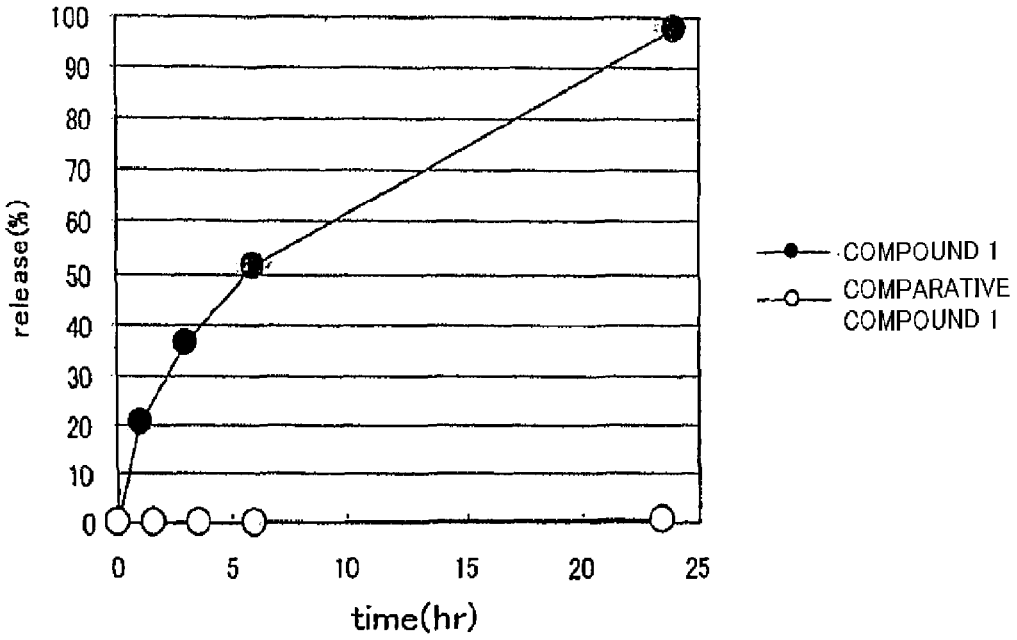
FIG. 1 illustrates a proportion of the amount of the released prednisolone based on the total amount of the prednisolone in the conjugate in PBS solution (pH 7.1; 37° C.) containing Compound 1 of the present invention (the high-molecular weight conjugate in which prednisolone is bonded to a polyaspartic acid moiety) or Comparative compound 1 (the high-molecular weight conjugate in which prednisolone is bonded to a polyglutamic acid moiety).
Figure 2:
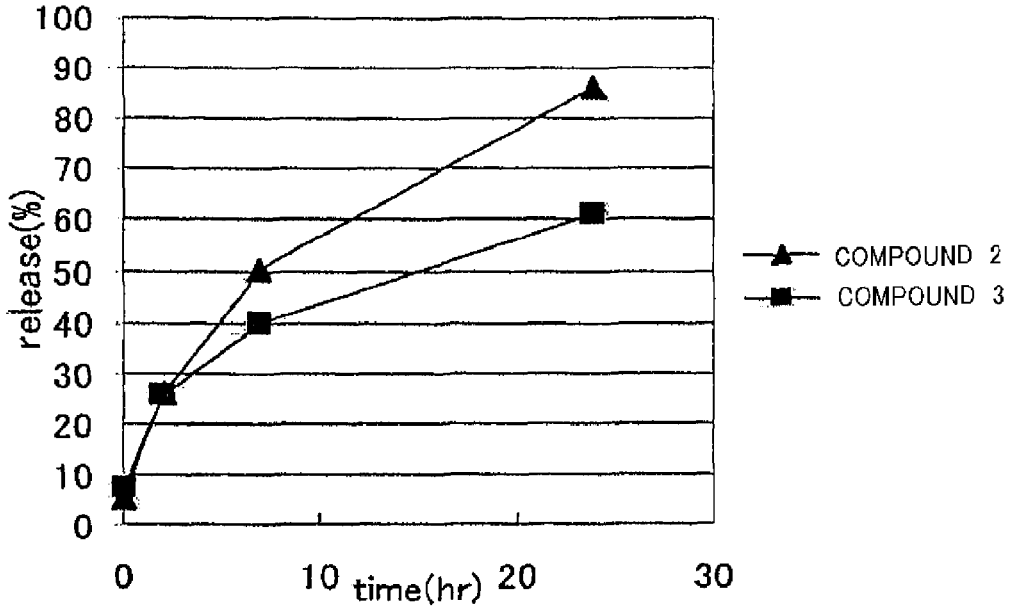
FIG. 2 illustrates a proportion of the amount of the released dexamethasone based on the total amount of the dexamethasone in the conjugate in PBS solution (pH 7.1; 37° C.) containing Compound 2 of the present invention (the high-molecular weight conjugate in which dexamethasone is bonded to a polyaspartic acid moiety) or Compound 3 of the present invention (the high-molecular weight conjugate in which dexamethasone and phenylalanine benzyl ester are bonded to a polyaspartic acid moiety).

The invention claimed is:

1. A high-molecular weight conjugate of steroids, comprising a structure in which a carboxylic acid group of a block copolymer having a polyethylene glycol moiety and polyaspartic acid is ester-bonded to an alcoholic hydroxy group in the steroids, and wherein the conjugate is represented by formula (I)

[

(I)

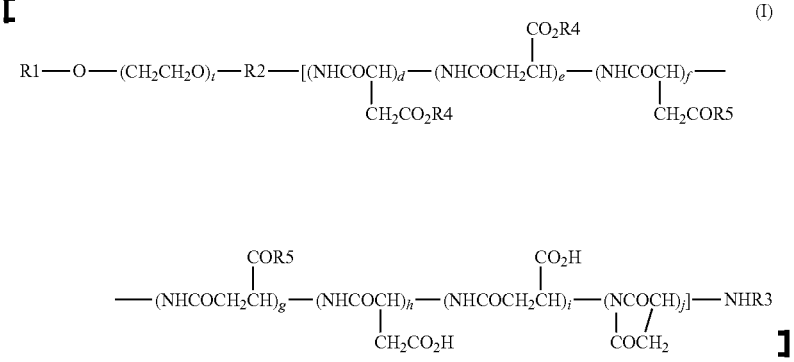

]

(I)

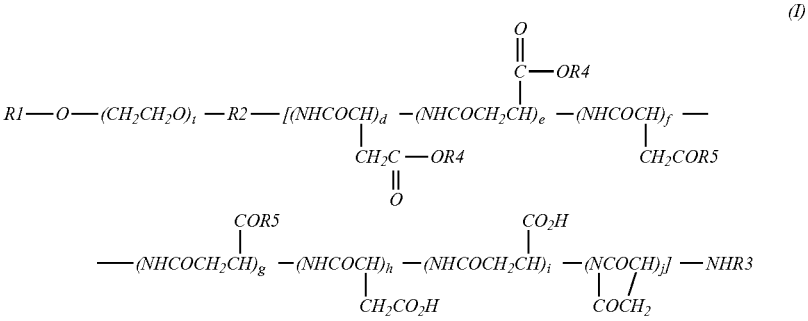

wherein R1 represents a (C1-C6) alkyl group; R2 represents a (C2-C6) alkylene group; R3 represents a (C1-C6) acyl group; [R4] —*OR4* represents an alcoholic hydroxy group of said steroids; R5 represents a group selected from the group consisting of a (C1-C30) alkoxy group, a (C7-C30) aralkyloxy group, a (C1-C30) alkylamino group, a di(C1-C30) alkylamino group, an amino acid with a protected carboxy group and —N(R6)CONH(R7) wherein R6 and R7, which may be identical or different from each other, represent a (C3-C6) cyclic alkyl group or a (C1-C5) alkyl group which may be substituted with a tertiary amine group; t represents an integer from 100 to 300; and d, e, f, g, h, i or j each independently represents an integer from 0 to 100; provided that d+e represents an integer from 1 to 100, d+e+f+g+h+i+j represents an integer from 6 to 100; and respective units of the polyaspartic acid are bonded in any order.

2. The high-molecular weight conjugate of steroids according to claim 1, wherein R1 represents a (C1-C3) alkyl group, R2 represents a (C2-C4) alkylene group, R3 represents a (C1-C3) acyl group, t represents an integer from 100 to 300, and d, e, f, g, h, i or j each independently represents an integer from 0 to 90, provided that d+e represents an integer from 1 to 90 and d+e+f+g+h+i+j represents an integer from 15 to 90.

3. The high-molecular weight conjugate of steroids according to claim 1 or 2, in which the steroids are prednisolone, methyl prednisolone, dexamethasone, betamethasone, clobetasol, diflorasone, diflucortolone, fluocinolone acetonide, hydrocortisone, difluprednate, beclometasone, triamcinolone or alclometasone.

4. A method of manufacturing the high-molecular weight conjugate of steroids described in claim 1, the method comprising ester-bonding a carboxylic acid group of a block copolymer having a polyethylene glycol moiety and polyaspartic acid to an alcoholic hydroxy group of the steroids, by using a dehydrating condensation agent in an organic solvent.

5. A pharmaceutical composition comprising as an active ingredient the high-molecular weight conjugate of steroids according to claim 1.

6. An anti-inflammatory agent comprising as an active ingredient the high-molecular weight conjugate of steroids according to claim 1.

7. An anti-rheumatism agent comprising as an active ingredient the high-molecular weight conjugate of steroids according to claim 1.

8. An agent for treating collagen disease comprising as an active ingredient the high-molecular weight conjugate of steroids according to claim 1.

9. An anti-allergy agent comprising as an active ingredient the high-molecular weight conjugate of steroids according to claim 1.

*10. The high-molecular weight conjugate of steroids according to claim 2, in which the steroids are prednisolone, methyl prednisolone, dexamethasone, betamethasone, clobetasol, diflorasone, diflucortolone, fluocinolone acetonide, hydrocortisone, difluprednate, beclometasone, triamcinolone or alclometasone.*

* * * * *